United States Patent [19]
Bonnet et al.

[11] Patent Number: 5,827,274
[45] Date of Patent: Oct. 27, 1998

[54] ELECTRODE FOR VAPORIZING TISSUE

[75] Inventors: Ludwig Bonnet, Knitltingen; Manfred Boebel, Oetisheim, both of Germany

[73] Assignee: Richard Wolf GmbH, Knittlingen, Germany

[21] Appl. No.: 678,278

[22] Filed: Jul. 11, 1996

[30] Foreign Application Priority Data

Jul. 18, 1995 [DE] Germany .................... 195 26 242.5

[51] Int. Cl.⁶ .................................................. A61B 17/36
[52] U.S. Cl. ................... 606/41; 606/45; 606/48; 606/49; 606/50; 606/46
[58] Field of Search ................. 606/32, 41, 44, 606/47, 48, 50, 51, 52, 45, 46

[56] References Cited

U.S. PATENT DOCUMENTS 5,354,296 10/1994 Turkel .
5,395,363 3/1995 Billings et al. .
5,549,605 8/1996 Hahnen ....................................... 606/47
5,582,610 12/1996 Grossi et al. .............................. 606/41

*Primary Examiner*—John P. Lacyk
*Assistant Examiner*—Rosiland Kearney
*Attorney, Agent, or Firm*—Panitch Schwarze Jacobs & Nadel, P.C.

[57] ABSTRACT

An electrode for vaporizing tissue is disclosed which has a head provided with projections and recesses and which is supported by at least one externally insulated electrically conducting branch. In order to provide a better and more effective electrode with regard to vaporization power and which can be easily cleaned and cheaply manufactured, the head which is rigidly fixed to the branch comprises essentially of part of a rotationally symmetrical body.

8 Claims, 1 Drawing Sheet

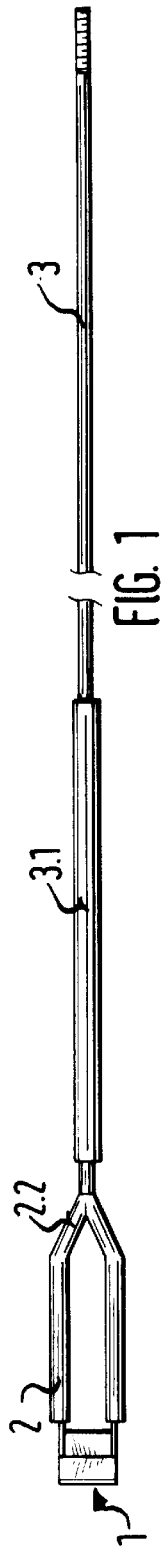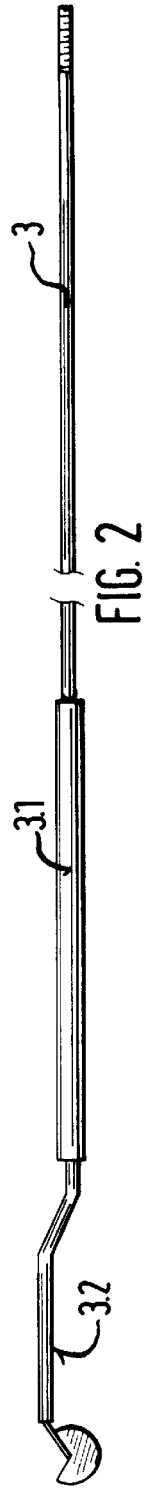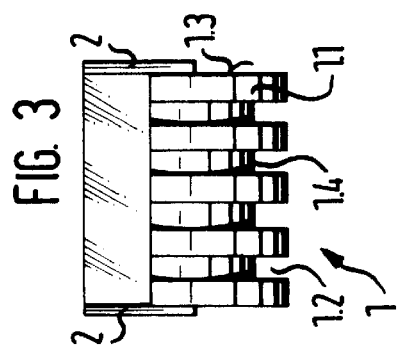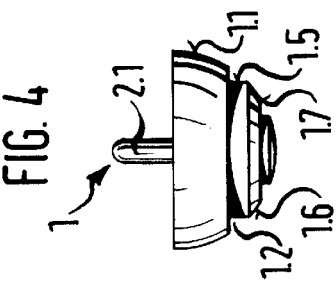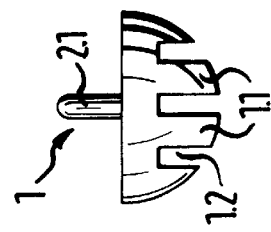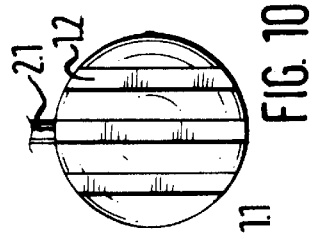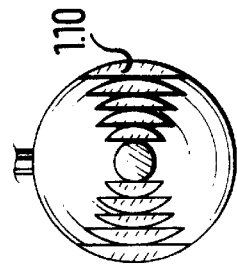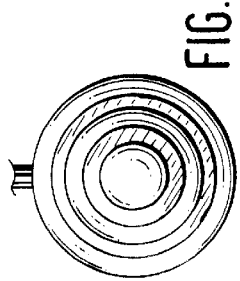

5,827,274

ELECTRODE FOR VAPORIZING TISSUE

BACKGROUND OF THE INVENTION

The invention proceeds from an electrode for vaporizing tissue having a head which is provided with projections and recesses and is supported by at least one externally insulated electrically conducting branch.

BRIEF DESCRIPTION OF THE PRIOR ART

Such electrodes with rotatably mounted heads in the form of rolls (DE-A-2 222 820, DE-C-4 242 126) are applied in order for example to remove adenomatous tissue by vaporization in combination with resectoscopes used in urology or also gynecology. For this purpose a high frequency voltage, produced by way of suitable high frequency generators and conducted via the branches, is applied to the electrodes, whereby the electrodes can by be operated in a bipolar or monopolar manner, according to the constructional type.

Such electrodes are, amongst other things disadvantageous in that the available electrical power cannot be transmitted via the bearing regions to the head which rolls on vaporization without losses and in that soiling in the bearing region is difficult to remove and limits the fuctioning of such electrodes. Moreover with such electrodes, the advantage of arranging many projections and edges on the electrode head leading to a corresponding multitude of locations at which the current with a high intensity can be transmitted from the electrode head to the tissue is not optimally exploited.

It is the object of the invention to provide an improved and very effective electrode with regard to the vaporization power and which may be easily cleaned and can be cheaply manufactured.

This object is achieved with an electrode of the previously described type in that the head which is rigidly fixed to the branch comprises essentially of part of a rotationally symmetrical body.

With the rigid electrical connection of the branch or branches to the head, no losses arise on the transfer of current to the head. Moreover from part of a rotationally symmetrical body, as for example from a cylinder, cone or spherical segment, by simple treatment, a relatively large number of projections and recesses can be made by machining, erosion or likewise, whereby the thus resulting high number of edges ensures that on vaporization, at relatively many locations of the head high current densities occur and that a good vaporization effect can be achieved.

Preferable designs of the head can be deduced from the dependent claims, whereby the mushroom-head type designed electrodes can be particularly also applied when merely groove shaped recesses in selected tissue sections are to be made, for example with * sclerosis, through which then urine can be drained from the bladder.

Finally, for the purpose of optimising the power transmission, at least the active part of the head can comprise a high conductable material, for example gold, or a corresponding surface layering can comprise such a material.

BRIEF DESCRIPTION OF THE DRAWINGS

The invention is hereinafter described in more detail by way of the embodiment examples shown in the figures. These show:

FIG. 1 a plan view of the vaporization electrode according to the invention,

FIG. 2 a lateral view of the vaporization electrode according to FIG. 1,

FIG. 3 an embodiment example of the head of the electrode,

FIG. 4 a further embodiment example of the head of the electrode,

FIG. 5 a view of the operating side of the head according to FIG. 4,

FIGS. 6 and 7 a further embodiment example of the head of the electrode,

FIG. 8 a view of the operating side of the head according to FIG. 7,

FIG. 9 a further embodiment example of the head of the electrode,

FIG. 10 a view of the operating side of the head according to FIG. 9.

DETAILED DESCRIPTION OF THE PREFERRED EMBODIMENTS

In accordance with FIGS. 1 and 2 the electrode, which is to be introduced into the shank of a resectocope which is not shown, comprises a head 1, at least one branch 2 carrying the head 1 and a connecting rod 3, which is made from electrically conducting material.

The heads 1 are each provided with projections 1.1 and recesses 1.2 and are attached to the branch or branches by soldering or welding. Two branches may form a fork shaped mounting for the head 1 in accordance with FIG. 2 and may continue proximally in the connecting rod 3, which at the same time serves as the electrical conduction for the head 1. The branches 2 are formed cranked, so that the connecting rods 3 each form approximately the centre of gravity of the head 1, and are provided with an external insulating layer 2.2 or 3.1 as is the connecting rod 3.

According to FIGS. 2 and 3 the head 1.3 is made from a sector of a solid cylinder, is connected at its end faces to the branches 2, and is provided on its circumference with radial slots 1.4 which can be formed by machining the cylinder sector, and which form the projections 1.1 and recesses 1.2, and leave adjacent web shaped regions.

According to FIGS. 4 to 10 the heads, finished for example from a hemisphere, have an essentialy mushroom-head type form, whereby the mounting is effected by a branch 2.1 which fixed to that side of the head 1 distant to the operating side in the region of the centre of said head, and running proximally is bent perpendicularly to the axis of the head 1.

With the embodiment according to FIGS. 4 and 5, the projections 1.1 and the recesses 1.2 are formed by step shaped concentric circumferential slots 1.5 which interrupt the circumference of the hemisphere and which with annular parts 1.6, form edges 1.7 at which current with a high density is transferred to the tissue.

The embodiment according to FIG. 6 comprises, as with the head according to FIGS. 4 and 5, radial circumferential step shaped slots 1.8 which are however arranged in such a sequence that the circumference of the hemisphere only remains in the form of circumferential edges 1.9. Otherwise such a head may also be manufactured by corresponding machining of a solid cylinder.

With the embodiments according to FIGS. 7 and 8, the projections 1.1 and recesses 1.2 are formed by steps 1.10 which result from parallel notches running transversly to the branch 2.1 and which are made on opposite sides of the head manufactured from a rotatory body, and which forms a multitude of edges which extend in an arch shaped manner over the periphery with the result of high current densities at these edges on vaporization.

Finally the design of the head according to FIGS. 9 and 10 are characterized in that the projections 1.1 and the recesses 1.2 are formed by groove shaped notches running parallel to the branch 2.1 and to each other, which, seen in the direction of the branch 2.1, give a comb shaped appearance, whereby the edges arising between the flanks of the notches and the circumference of the head, seen transversely to the branch 2.1, run in an arch shaped manner when the head is for example made from part of a spherical body or has a straight course when the head is made for example from part of solid cylinder.

We claim:

1. An electrode for vaporizing tissue comprising a head (1) supported by at least one externally insulated electrically conducting branch (2), the head (1) being a sector of a solid cylinder (1.3) rigidly fixed to the branch (2) and including parallel projections (1.1) and recesses (1.2) which are oriented generally perpendicularly to an axis of the cylinder.

2. An electrode according to claim 1, wherein the branch or branches (2) is/are bent on that side of the head (1) distant to the operating side and essentially at right angles to the axis of the head and running at a slight distance to the head.

3. An electrode according to claim 1, wherein the projections (1.1) and the recesses (1.2) run parallel to the branch or branches (2).

4. An electrode according to claim 1, wherein at least the active part of the head (1) consists of a high conductable material or comprises a surface layering of such a material.

5. An electrode for vaporizing tissue comprising a head (1) supported by at least one externally insulated electrically conducting branch (2), the head (1) being formed with a mushroom-shape and including projections (1.1) and recesses (1.2) on a circumference of the head, the mushroom-shape comprises a portion of a spherical surface.

6. The electrode of claim 5 wherein the head is hemispherical.

7. An electrode according to claim 5, wherein the projections (1.1) and the recesses (1.2) run parallel.

8. An electrode according to claim 5, wherein the projections (1.1) and the recesses (1.2) are formed by step shaped surface geometry of the head (1).

* * * * *